United States Patent [19]

Saleh et al.

[11] Patent Number: 4,864,036

[45] Date of Patent: Sep. 5, 1989

[54] PROCESS FOR PREPARING AROMATIC CARBOXYLIC ANHYDRIDE

[75] Inventors: Ramzi Y. Saleh, Neshanic Station; Isreal E. Wachs, Bridgewater, both of N.J.

[73] Assignee: Exxon research & Engineering Company, Florham Park, N.J.

[21] Appl. No.: 213,524

[22] Filed: Jun. 30, 1988

Related U.S. Application Data

[60] Continuation-in-part of Ser. No. 796,707, Nov. 12, 1985, Pat. No. 4,791,092, which is a division of Ser. No. 626,405, Jun. 29, 1984, Pat. No. 4,582,911.

[51] Int. Cl.$^4$ ............................................. C07D 307/89
[52] U.S. Cl. .................................. 549/239; 549/236; 549/245; 549/248; 549/253; 549/259; 549/258
[58] Field of Search ............... 549/236, 239, 245, 248, 549/253, 257, 258

[56] References Cited

U.S. PATENT DOCUMENTS

| | | | |
|---|---|---|---|
| 4,582,911 | 4/1986 | Wachs et al. | 549/239 |
| 4,582,912 | 4/1986 | Saleh et al. | 549/239 |
| 4,728,744 | 3/1988 | Saleh et al. | 539/239 |

Primary Examiner—Richard L. Raymond
Attorney, Agent, or Firm—J. J. Mahon; M. S. Goodwin

[57] ABSTRACT

In accordance with the process of this invention, an improved catalyst for molecular oxidation of a hydrocarbon to form the corresponding carboxylic anhydrides is prepared by the steps of (a) forming a catalyst precursor by depositing on titanium dioxide solids in the anatase form a discontinuous monolayer amount of at least one source of a Group VIB metal oxide; (b) calcining the thus-formed catalyst precursor under conditions sufficient to convert the Group VIB metal oxide source into the corresponding group VIB metal oxide; (c) depositing upon the calcined catalyst precursor a catalytically effective amount of at least one vanadium oxide source which is convertible into vanadium oxide upon heating; and (d) calcining the vanadium-deposited solids under conditions sufficient to convert the vanadium compound into vanadium oxide.

18 Claims, 1 Drawing Sheet

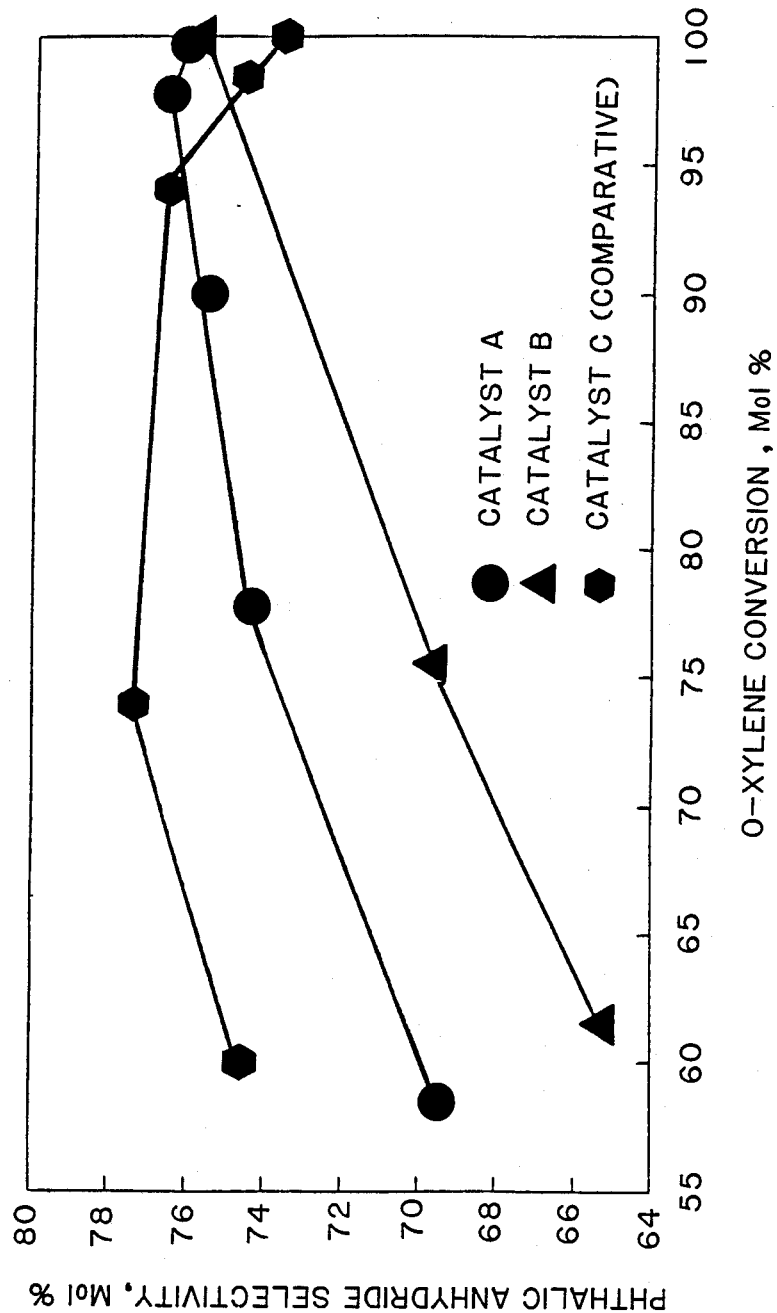

4,864,036

PROCESS FOR PREPARING AROMATIC CARBOXYLIC ANHYDRIDE

This is a continuation-in-part application of pending application Ser. No. 796,707, filed Nov. 12, 1985, now U.S. Pat. No. 4,791,092, which is a divisional application of Ser. No. 626,405 filed June 29, 1984, issued Apr. 15, 1986 as U.S. Pat. No. 4,582,911.

BACKGROUND OF THE INVENTION

This invention relates generally to the manufacture of carboxylic anhydrides, and more particularly to novel catalysts and methods for their use in manufacturing carboxylic anhydrides by molecular oxidation of hydrocarbon feedstocks, in particular the manufacture of phthalic anhydride by molecular oxidation of orthoxylene.

Aromatic carboxylic anhydrides are widely produced in large quantities through the molecular partial oxidation of hydrocarbon feedstocks, particularly phthalic anhydride from orthoxylene. The phthalic anhydride product is commercially useful for reactions with alcohols, such as oxo-alcohols to form the corresponding phthalic anhydride alcohol esters, which find use as plasticizers and lubricants.

Catalysts for the above partial oxidation, in which vanadium pentoxide is deposited on titania, are known in the art. The art has sought to develop improved and promoted catalysts in order to enhance the activity and selectivity for the phthalic anhydride fraction.

U.S. Pat. Nos. 3,464,930, 3,509,179, 3,684,741 and 3,909,457, and British Pat. Nos. 1,140,264 and 1,237,954, to BASF disclose catalysts prepared by depositing vanadium pentoxide-titanium dioxide on a carrier which is optionally primed with an oxide of the metals vanadium, molybdenum, tungsten, cobalt, zirconium, chromium, titanium, iron or mixtures thereof.

See also S. Matsuda et al., *Applied Catalysis*, 8 (1983) 149–165, for discussion of titanium dioxide catalysts in general, including mixed oxides composed of $TiO_2$ and $MoO_3$.

U.S. Pat. Nos. 4,052,418 (1977) and 4,234,461 (1980) to Standard Oil Company illustrate a promoted catalyst in which the vanadium pentoxide is admixed with an oxide of at least one of the group of boron, niobium, tantalum, antimony, tungsten and chromium (with or without one or more of the group of alkaline metals, zinc, cadmium, phosphorus, arsenic, copper, cerium, thorium, tin, manganese, iron and uranium). The catalysts are prepared by digesting the vanadium pentoxide and the selected promoter oxide in hydrochloric acid followed by drying at 120° C. See also U.S. Pat. Nos. 4,075,231 and 4,076,731 to Standard Oil Company which disclose oxide catalysts containing molybdenum or tungsten among other metals. U.S. Pat. No. 4,293,449 (1981) to Standard Oil Company describes a high surface area catalyst consisting of a support material such as silica, alumina, alumina-silica, silicon carbide, titania and zirconia and a high-surface area coating to which is applied solutions of ammonium heptamolybdate, ammonium hydroxide or cobalt nitrate.

U. K. Published Application No. 640,555 describes an oxidation catalyst comprising a ground layer and surface layer wherein in both layers ferric oxide may be replaced in whole or in part by other oxides such as chromium or manganese sesquioxide, vanadium sesquioxide, cobalt oxide, thorium oxide or other of the transition metals.

U.S. Pat. No. 3,721,683 (1973) to Teijin Chemicals Limited discloses catalysts obtained by calcining a mixture of a vanadium compound, a chromium compound, and a promoter metal component, the vanadium and chromium being present in an atomic ratio of 1:0.5 to 1:1.

Vanadium pentoxide monolayer catalysts have been studied and discussed in A. J. Van Hengstum et al., *Applied Catalysis*, Vol. 8, 369–382 (1983); M. Gasior et al., *Applied Catalysis*, vol. 10, 87–100 (1984); G. C. Bond et al., *Faraday Discussions of the Chemical Society*, vol. 72, 235–246 (1981), and G. C. Bond et al., *Journal of Catalysis*, vol. 77, 309–322 (1982).

Commonly-assigned U.S. Pat. No. 4,582,911 discloses phthalic anhydride catalysts prepared by the steps of forming a catalyst precursor by depositing on titanium dioxides solids in the anatase form a discontinuous monolayer amount of at least one source of tantalum oxide, calcining the thus-formed catalyst precursor under conditions sufficient to convert the tantalum oxide source into the oxide form, depositing upon the calcined catalyst precursor a catalytically effective amount of at least one vanadium compound which is convertible into vanadium oxide upon heating and calcining the vanadium-deposited solids under conditions sufficient to convert the vanadium compound into vanadium oxide.

Commonly-assigned U.S. Pat. No. 4,582,912 discloses a phthalic anhydride catalyst prepared from sources of vanadium oxide, titanium oxide and the oxide of a promoter metal selected from Sb, Ga, Ge, In, Tl, Pb, Se, Te, P and Bi. The catalyst is prepared by a process of sequential deposition wherein at least a continuous monolayer amount of a vanadium oxide source is first deposited on $TiO_2$ anatase to form a catalyst precursor which is then calcined; and thereafter a vanadium oxide source and the oxide of at least one of the aforementioned reactive metals are deposited on the calcined catalyst precursor, the resulting catalyst solids then being calcined.

Commonly-assigned U.S. Pat. No. 4,728,744, which is also hereby incorporated by reference, discloses a sequential deposition process for forming a zirconia based catalyst wherein a source of zirconium oxide is deposited in an amount sufficient to provide a continuous monolayer on titanium dioxide solids in the anatase form; the thus-formed catalyst precursor is then calcined; and a source of vanadium oxide is then deposited on the calcined catalyst precursor; and the catalyst is again calcined.

The catalysts in the foregoing commonly-assigned patents may also comprise effective amounts of promotor metal oxides selected from the group consisting of niobium, magnesium, calcium, scandium, yttrium, lanthanium, uranium, cerium, chromium, magnanese, iron, cobalt, nickel, copper, zinc, aluminum, gallium, indium, silicon, germanium, tin, bismuth, antimony, tellurium, lead, hafnium, alkali metals (Cs, Rb, K, Na, Li) and mixtures thereof.

SUMMARY OF THE INVENTION

In accordance with the process of this invention, an improved titania-based catalyst for molecular oxidation of hydrocarbons to form the corresponding carboxylic anhydrides is prepared by the steps of forming a catalyst precursor by depositing on titanium dioxide solids in the anatase form a discontinuous monolayer amount of at least one source of an oxide of a metal selected from the metals of Group VIB of the Periodic Table which comprise the chromium group (i.e. chromium, molybdenum or tungsten, which are hereinafter referred to as Group VIB metals); calcining the thus-formed catalyst precursor under conditions sufficient to convert the Group VIB metal oxide source into the oxide form; depositing upon the calcined catalyst precursor a catalytically effective amount of at least one vanadium compound which is convertible into vanadium oxide upon heating; and calcining the vanadium-deposited solids under conditions sufficient to convert the vanadium compound into vanadium oxide.

DETAILED DESCRIPTION OF THE INVENTION

This invention relates to improved catalysts for the manufacture of carboxylic anhydrides by catalytic oxidation of hydrocarbons and relates more particularly to an improved process for producing aromatic carboxylic anhydrides such as phthalic anhydride and pyromellitic dianhydride by reacting a mixture of an oxygen-containing gas and an aromatic hydrocarbon (such as orthoxylene or naphthalene) in vapor phase in the presence of a novel catalyst therefor.

Catalyst Preparation

The improved catalyst of this invention is prepared by a four-step procedure, in which there is first deposited on titanium dioxide in the anatase form, an oxide of at least one Group VIB metal or at least one source of such oxide, followed by calcining of this catalyst precursor to form a calcined catalyst precursor. The calcined catalyst precursor is then treated in a second deposition step with the selected amount of a vanadium oxide source, and optionally catalyst promoters, followed by calcining in a separate calcining step to obtain the desired improved anhydride catalyst.

Suitable sources of the Group VIB metal oxide are compounds and complexes which are convertible to the oxide upon heating to the calcination temperatures in the first calcination step.

Suitable chromium compounds include chromic acid, ammonium dichromate, chromium halides, chromium nitrate, chromium perchlorate, chromium sulfate and chromium pentadionate.

Suitable molybdenum compounds include ammonium heptamolybdate, molybdenum halides and molybdenum oxyhalides.

Suitable tungsten compounds include ammonium metatungstate, tungsten halides and tungsten oxyhalides.

The selected Group VIB metal oxide source can be dry mixed with the titanium dioxide or deposited on the titanium dioxide from solutions or suspensions of the above-indicated metal oxide sources, for example, using aqueous or organic solvents. Illustrative organic solvents include formamide, diethyl acetamide, ammonium thiocyanate, molten urea or an alcohol. The solutions can be sprayed onto the titanium dioxide solids (for example, in a coating drum which has been preheated to from 150° to 450° C.) or impregnated thereon using conventional techniques.

If wet techniques are used to deposit the Group VIB metal oxide source, the wetted solids can then be conveniently dried in air (or under an inert atmosphere such as nitrogen) to at least partially remove the solvent prior to calcination. Drying can be achieved by exposing the catalyst precursor to air at room temperature for a period of from about 1 to about 100 hours or by placing it in a forced hot air oven maintained at a temperature of less than about 180° C., typically between about 60° and about 150° C. for about 1 to about 16 hours. Alternatively, the precursor can be air dried at room temperature for between about 1 and about 48 hours and then placed in the forced hot air oven. Drying of the catalyst precursor preferably should be conducted at temperatures below which crystal phase transitions occur and until a level of nearly constant weight is achieved. Drying under reduced pressure at room or elevated temperature, as described above, can also be employed as a suitable alternative.

The thus-formed catalyst precursor is then, according to the process of this invention, calcined under conditions sufficient to convert the Group VIB metal oxide source into the oxide form and to cause the metal oxide to be strongly attached to the surface of the titanium dioxide. Generally, a temperature of from about 100° to 750° C. will be sufficient, and temperatures of from 300° to 600° C. are preferred, and a time of calcination will range generally from 0.5 to 16 hours, with a time of from 1 to 5 hours being preferred. The precise temperature and time of calcination will depend upon the particular Group VIB metal oxide source which has been selected for use, and should be such as to avoid substantial crystal phase transformations of the $TiO_2$ anatase into another crystalline form, e.g., rutile.

The calcination can be performed, as is preferred, in air or in the presence of an $O_2$-containing gas. Although not essential, it is desirable to maintain a steady flow of the chosen atmosphere over the catalyst precursor surface during calcination. Flow rates typically will be sufficient to provide a contact time with the catalyst of about 1 to about 10, preferably from about 1 to about 5, and most preferably from about 1 to about 3 seconds. Thus, suitable flow rates or space velocities of the calcining atmosphere may be manipulated by one skilled in the art to achieve the desired contact time.

The titanium dioxide which is employed is preferably in the anatase form. Preferably at least about 25 wt. % (and most preferably from about 50–100 wt. %) of the titanium dioxide is in the anatase form. The titanium dioxide may be prepared by any conventional technique, for example the techniques described in R. J. H. Clark, "The Chemistry of Titanium and Vanadium", p. 267 (Elsevier Publishing Co., 1968).

The titanium oxide used in the catalyst of this invention is composed of substantially porous particles of a diameter of from about 0.4 to 0.7 micron and is preferably of a specific surface area of from 1 to 25 $m^2/g$ which are essentially aggregated masses of primary particles.

The particle diameter of the primary particles can be measured by a mercury penetration-type porosimeter. When using porous titanium oxide consisting of primary particles having a particle diameter in the range of 0.005 to 0.05 micron, the concentration of the slurry is 5 to 25% by weight, preferably 10 to 20% by weight. When using porous titanium oxide consisting of primary particles having a particle diameter of 0.05 to 0.4 micron, the slurry concentration is 10 to 40% by weight, preferably 15 to 25% by weight.

Depending upon the raw ore, the $TiO_2$ may include iron, zinc, aluminum, manganese, chromium, calcium, lead, silicon, etc. These incidental elements are not detrimental to the reaction if their total amount is less than 0.5% by weight based on $TiO_2$. Therefore, the TiO$_2$ can comprise pigment grade anatase, and no special purification procedure is required.

It has been found that improved phthalic anhydride selectivities and yields are obtained when a discontinuous monolayer of at least one Group VIB metal oxide is present on the titanium dioxide catalyst solids. Therefore, the quantity of the Group VIB metal oxide source which is contacted with the titanium dioxide catalyst solids should provide a discontinuous monolayer of Group VIB metal oxide on the titanium dioxide catalyst solids.

In order to form a discontinuous monolayer on the titanium dioxide catalyst solids, the selected Group VIB metal oxide source will be provided in an amount sufficient to provide from about 0.05 wt. % to 1.0 wt. %, and more preferably from 0.10 wt. % to 0.50 wt. % of Group VIB metal oxide.

Without being bound thereby, it is believed that the deposition of a discontinuous monolayer of Group VIB metal oxide on the titania so modifies the titania surface that the finally prepared catalyst, obtained after the subsequent deposition of the vanadium oxide source and the second calcination step, stabilizes the titania surface (perhaps by locking up TiO$_2$ surface defects) to minimize the reaction of vanadia and titania. It has been observed that the vanadia can react with the bulk TiO$_2$ anatase to form a solid phase of titania and V oxide, $V_xTi_{1-x}O_2$ (wherein x is from 0 to 0.08), which has been observed to have a negative effect on the overall selectivity to the desired anhydride product. This reaction of the vanadia and titania has been observed in the laboratory to occur at a slow rate at temperatures in excess of 500° C., and at a greatly accelerated rate at temperatures of greater than 575° C., in the case of catalysts prepared by prior art methods, in which the TiO$_2$-anatase is not first modified by the method of this invention.

The intermediate calcining step, in preparing the catalyst precursor, is believed to be necessary in order to cause the Group VIB metal oxide to form the necessary bond with the TiO$_2$ surface. It is believed that the selected Group VIB metal oxide source is adsorbed (physically or both physically and chemically) onto the surface of the TiO$_2$ and that the calcining step converts the Group VIB metal oxide source to the oxide, which is chemically adsorbed on the TiO$_2$ surface.

The resulting calcined catalyst precursor solids are then treated in a separate step to deposit thereon a source of vanadium oxide and optionally a reactive metal source such as is disclosed in U.S. Pat. No. 4,582,912, followed by calcining in a separate step.

The vanadium metal oxide source may be vanadium pentoxide but is preferably a vanadium compound such as an ammonium metavanadate, vanadyl sulfate, vanadyl halide (e.g., vanadyl chloride, vanadyl dichloride), vanadyl oxyhalide (e.g., vanadyl oxychloride), metavanadic acid, pyrovanatic acid, vanadium hydroxide, and vanadyl carboxylates such as formate, tartrate, salicylate and oxalate, which can then become vanadium oxide at the calcining temperature. The vanadium compounds most convenient for the catalyst preparation are V$_2$O$_5$ and vanadyl oxalate.

The selected vanadium oxide source can be deposited on the calcined catalyst precursor from solutions or suspensions of the vanadium oxide source, for example using aqueous or organic solvents. Illustrative organic solvents include formamide, diethyl/acetamide, ammonium thiocyanate, molten urea or an alcohol. The solutions can be sprayed onto the calcined catalyst precursor solids (for example in a coating drum which has been preheated to from 150° to 450° C.) or impregnated thereon using conventional techniques.

If wet techniques are used, the wetted solids can then be dried in air or under an inert atmosphere (such as nitrogen) as described previously, conveniently at a temperature of from 50° to 200° C., followed by calcining for activation of the catalyst at a temperature of from 100° to 650° C., preferably 350° to 550° C., and for about 0.5 to 16 hours, preferably 1 to 5 hours. The precise conditions of calcining will vary depending upon the vanadium oxide source which is employed and should be sufficient to convert the vanadium compound into the vanadium oxide. Again, the conditions of calcining should be such as to avoid substantial crystal phase transformation of the TiO$_2$ anatase into another crystalline form, e.g. rutile.

The thus-prepared catalyst will contain generally from about 0.7 to 50 wt. % of vanadium oxides, calculated as V$_2$O$_5$, and the mole ratio of vanadium to Group VIB metal oxide is from about 5:1 to 20,000:1, and preferably from about 10:1 to 2,000:1, gram atoms of vanadium (calculated as vanadium) per gram atom of Group VIB metals (calculated as the metal).

The precise quantity of the selected V source which is used in the V deposition step can therefore vary but preferably should be sufficient to provide full coverage of the exposed TiO$_2$ surface; that is, to provide at least a mono-layer of V$_2$O$_5$ on the portions of the TiO$_2$ surfaces in the calcined catalyst precursor not previously covered by the Group VIB metal oxide discontinuous monolayer. The minimum quantity of V$_2$O$_5$ to be provided will generally correspond to the expression (I):

$$A\ N_{min} = (G) \times (A') \times (k') \qquad (I)$$

wherein "$N_{min}$" is the weight in grams of V$_2$O$_5$ to be adsorbed as described herein on the calcined catalyst precursor, "G" is the weight in grams of the calcined catalyst precursor, "A" is the specific surface area (BET) of the calcined catalyst precursor and "k" is the number of grams of V$_2$O$_5$ required to form a continuous monolayer of V$_2$O$_5$ on 1 gram of calcined precursor having a specific surface area of 1 m$^2$/gm.

For calcined catalyst precursors having a specific surface area of from 1 to 25 m$^2$/gm, the value of "k" in expression (I) is 0.0007. Therefore, expression (I) reduces to $$A\ N_{min} = (G) \times (A') \times (0.0007) \qquad (II)$$

for such calcined catalyst precursors. However, since the formation of the Group VIB metal oxide discontinuous monolayer does not significantly alter the specific surface area (A) of the TiO$_2$, expression (II) can be further reduced to:

$$N_{min} = (G) \times (A') \times (0.0007) \qquad (III)$$

wherein $N_{min}$ and G are as defined previously, and A' is the specific surface area in M$^2$/gm (BET surface area) of the TiO$_2$ to be treated.

The grams of the selected V oxide source (calculated as its V$_2$O$_5$ equivalent weight) employed in this invention will preferably comprise at least about 1.7 $N_{min}$, and more preferably from about 2.5 $N_{min}$ to 50 $N_{min}$, (wherein $N_{min}$ is calculated as in expression (III) in order to ensure complete coverage of the $TiO_2$ surfaces of the calcined catalyst precursor, since it has been observed that exposed $TiO_2$ surface on the catalyst hereinafter. (Greater than 50 $N_{min}$ can be used if desired, but generally provides no pronounced further benefit.) The presence of more than a monolayer of $V_2O_5$ can be observed by examining the $TiO_2$ catalyst surface for evidence of $V_2O_5$ crystallites, which are believed to comprise the $V_2O_5$ species which forms when $V_2O_5$ is used in excess of the $V_2O_5$ monolayer amount. Such a surface examination for $V_2O_5$ crystallites can be conducted using Laser Raman Spectroscopy, as described in F. Roozeboom et al., *J. Phys. Chem.*, vol. 84, p. 2783, (1980).

The surface area of the activated unsupported catalyst can vary typically from about 1 to about 25 $m^2/g$.

Surface areas herein are determined by the BET method, the general procedures and theory for which are disclosed in H. Brunaur, P. Emmett, and E. Teller, *J. of Am. Chem. Soc.*, Vol. 60, p. 309 (1938).

The catalyst can further comprise effective amounts of promoter metal oxides selected from the group consisting of niobium, magnesium, calcium, scandium, yttrium, lanthanum, uranium, cerium, chromium, manganese, iron, cobalt, nickel, copper, zinc, aluminum, gallium, indium, silicon, germanium, tin, bismuth, antimony, tellurium, lead, hafnium, zirconium, alkali metals (Cs, Rb, K, Na, Li) and mixtures thereof.

The promoters and/or activators are readily introduced into the catalyst during deposition of vanadium on the catalyst precursor by admixture with the vanadium compounds during the heating. These promoter and activator compounds, however, should be at least partially soluble in any solvent medium used in the particular preparation in order to be best suited for combination with the vanadium components of the catalyst.

Typical compounds of zinc (illustrative of activators as a class) are metallic zinc, zinc oxide, zinc chloride, zinc bromide, zinc iodide, zinc formate, zinc nitrate or zinc acetate. Generally, phosphorus compounds are used which have as the cation an ion which is more volatile than the phosphate anion. Various compounds may be used, such as metaphosphoric acid, triphosphoric acid, pyrophosphoric acid, orthophosphoric acid, phosphorus pentoxide, phosphorus oxyiodide, ethyl phosphate, methyl phosphate, amine phosphate, phosphorus pentachloride, phosphorus trichloride, phosphorus oxybromide, and the like. The alkali metal may suitably be introduced by employing alkali metal compounds such as alkali metal salts with examples being lithium acetate, lithium bromide, lithium carbonate, lithium chloride, lithium hydroxide, lithium iodide, lithium oxide, lithium sulfate, lithium orthophosphate, lithium metavanadate, potassium sulfate, potassium chloride, potassium hydroxide, sodium chloride, sodium hydroxide, rubidium nitrate, cesium chloride and the like. Mixtures of two or more alkali metal compounds may be used, such as a mixture of lithium hydroxide and sodium chloride or a mixture of lithium chloride and potassium chloride. The preferred alkali metal elements are lithium, sodium and potassium, and mixtures thereof, with lithium being particularly preferred. The alkali metal compound will preferably be an alkali metal compound which either has a phosphate anion as the anion, that is a compound such as lithium phosphate, or a compound which has an anion which is more volatile than the phosphate anion.

These promoter metal oxides (or metal compounds which are sources for such oxides under calcination conditions) can be generally added to the catalyst solids by depositing on the calcined catalyst precursor with the vanadium. The amount of such promoter metal oxides which is employed in the catalyst can vary widely and will generally comprise from about 0.05 to 20 wt. % of the finally calcined catalyst, calculated as the corresponding promoter metal oxide. This will generally correspond to an atomic promoter metal oxide:-vanadium ratio of from 5:1 to 500:1, wherein the vanadium content is calculated as vanadium pentoxide.

The resulting finally calcined catalyst can be employed as such or deposited (as is preferred) on an inert catalyst carrier such as silicon carbide, silicon nitride, carborundum, steatite, alumina, alundum, and the like.

At some point in their preparation, the catalysts described herein preferably are formed into structures suitable for use in a reactor, although unshaped, powder catalysts can be employed. Techniques for forming the appropriate structures for use in a fixed bed reactor or a fluidized bed reactor are well known to those skilled in the art.

For example, the catalyst can be structured in unsupported form for use in fixed bed reactors by prilling or tableting, extruding, sizing and the like. Suitable binding and/or lubricating agents for pelleting or tableting include Sterotex ®, starch, calcium stearates, stearic acid, Carbowax, Methocel ®, Avicel ® and graphite and the like. Extrusion or pelleting of the catalyst can be achieved by forming a wet paste.

Supported catalysts for use in either fixed or fluidized bed operations employ carriers including alumina, silica, silica gel, silica-alumina, silicon carbide, ceramic donuts, magnesium oxide, titania and titania-silica. Spray dried catalysts can also be employed for fluidized bed operations.

A catalyst support, if used, provides not only the required surface for the catalyst, but gives physical strength and stability to the catalyst material. The carrier or support typically possesses a surface area of from about 0.1 to about 200 $m^2/g$, preferably from about 1 to about 50 $m^2/g$, and most preferably from about 5 to about 30 $m^2/g$. A desirable form of carrier is one which has a rough enough surface to aid in retaining the catalyst adhered thereto during handling and under reaction conditions. The support may vary in size but generally is from about 2½ mesh to about 10 mesh in the Tyler Standard screen size. Alundum particles as large as ¼ inch are satisfactory. Supports much smaller than 10 to 12 mesh normally cause an undesirable pressure drop in the reactor, unless the catalysts are being used in a fluid bed apparatus.

The support material is not necessarily inert, that is, the particular support may cause an increase in the catalyst efficiency by its chemical or physical nature or both.

The amount of the catalyst deposited on the support is usually in the range of about 5 to about 90% by weight, preferably from about 5 to about 80% by weight based on the combined weight of catalyst and support. The amount of the catalyst deposited on the support should be enough to substantially coat the surface thereof and this normally is obtained with the ranges set forth above. With more absorbent carriers, larger amounts of material will be required to obtain essentially complete impregnation and coverage of the carrier. In a fixed bed process, the final particle size of the catalyst particles which are coated on a support will also preferably be about 2½ to about 10 mesh size. While the supports may be of a variety of shapes, the preferred shape of the supports is in the shape of cylinders or spheres.

The particle size of a supported or unsupported catalyst used in fluidized beds is quite small, usually varying from about 10 to about 200 microns.

Inert diluents such as silica may be present in the catalyst, but the combined weight of the essential active ingredients of $TiO_2$, Group VIB metal oxide, and vanadium, should preferably consist essentially of at least about 5 wt %, preferably at least about 15 wt %, based on the total weight of catalyst and support.

Shaping of unsupported catalyst can be conducted prior or subsequent to calcination of the V-deposited catalyst precursor. Preferably, shaping of the unsupported catalyst is conducted on the catalyst precursor prior to deposition of V thereon. The point during which shaping with supports or carriers is conducted will vary with the type of support.

Solid supports, such a silica alumina, can be added to the reaction mixture during the formation of the catalyst precursor.

Vapor Phase Oxidation of Hydrocarbons

The catalysts of the present invention can be used to at least partially oxidize hydrocarbons to their corresponding carboxylic anhydrides. Such hydrocarbons which can be utilized in conjunction with the catalysts described herein comprise alkanes, typically alkanes of from 4 to about 10, preferably from about 4 to about 8, most preferably from about 4 to about 6 carbons; alkenes, typically alkenes of from about 4 to about 10, preferably from about 4 to about 8, most preferably from about 4 to about 6 carbons; cycloalkanes or cycloalkenes, typically cycloalkanes or cycloalkenes of from about 4 to about 14, preferably from about 6 to about 12, and most preferably from about 6 to about 10 carbons; alkyl substituted and unsubstituted aromatic compounds wherein the aryl portion thereof contains typically from about 6 to 14, preferably from about 6 to about 10 (e.g., 6) carbons and the alkyl portion contains typically from about 1 to about 10, preferably from about 1 to about 5 carbons, and mixtures thereof.

Representative examples of suitable alkanes include butane, pentane, isopentane, hexane, 3-methyl pentane, heptane, octane, isooctane, decane and mixtures thereof.

Representative examples of suitable alkenes include butene-1, butene-2 (cis or trans), 3-methylbutene-1, pentene-1, pentene-2, hexene-1, 3,3-dimethylbutene-1, 3-methyl-pentene-2, butadiene, pentadiene, cyclopentadiene, hexadiene, and mixtures thereof. It is also contemplated to use refinery streams rich in alkenes, particularly streams containing 70 percent or more butenes.

Representative examples of cycloalkanes which can be methyl substituted, include cyclobutane, cyclopentane, methyl-cyclopentane, cyclohexane, methylcyclohexane, 1,4-dimethyl-cyclohexane, cycloheptane, and cyclooctane. Mixtures of hydrocarbons rich in alkanes and cycloalkanes having between 4 and 10 carbon atoms, i.e., containing about 70 weight percent or more alkanes and cycloalkanes can also be used.

Representative examples of suitable aromatic compounds include benzene, toluene, xylene, cumene, pseudocumene, durene and mixtures thereof.

Heterocyclic compounds such as furan, benzofuran, thiophene can be employed. Also suitable and readily available are naphthas obtained from paraffiic or naphthenic petroleum sources. Full boiling range naphthas (boiling within the range of about 35°–230° C.) can be used but it is preferred to use light naphtha cuts boiling within the range of about 35°–145° C. The naphthas usually contain about 5–15 percent benzene and alkylbenzenes. It will be understood that other mixtures can be used, such as a paraffinic raffinate from the glycol-water solvent extraction of reformates.

Thus, the catalyst of the present invention can be used to convert butane or butene to maleic anhydride; isopentane or isopentene to citraconic anhydride, maleic anhydride and carboxy maleic anhydride; pseudocumene to trimetallitic anhydride; durene to pyromellitic anhydride; and orthoxylene and naphthalene to phthalic anhydride.

Preparation of Phthalic Anhydride

A preferred hydrocarbon feed for the catalyst of this invention for conversion to phthalic anhydride is orthoxylene, or an aromatic feedstream comprising a predominant amount of orthoxylene and more preferably at least 10 mol. % orthoxylene. In the following discussion and exemplification, therefore, orthoxylene is used in most examples to demonstrate (but not to limit) the use of catalysts made by the process of this invention for producing phthalic anhydride. (It will be understood, for example, that naphthalene can also be employed as a hydrocarbon feed to prepare phthalic anhydride.)

The oxidation of orthoxylene to phthalic anhydride may be accomplished by contacting orthoxylene in low concentrations with oxygen in the presence of the described catalyst. Air is entirely satisfactory as a source of oxygen, but synthetic mixtures of oxygen and diluent gases, such as nitrogen, carbon dioxide and the like also may be employed. Air enriched with oxygen may be employed. The oxygen-containing gas feed (e.g., air) is preferably preheated (e.g., to from 100°–300° C.) before introducing it into the reactor.

The gaseous feedstream to the oxidation reactors normally will contain air and typically from about 0.5 to about 10, preferably from about 1 to about 8, and most preferably from about 1.2 to about 5, mol. % orthoxylene. About 1.0 to about 1.9 mol. % of the orthoxylene in air is satisfactory for optimum yield of product for the process of this invention using a fixed bed reactor, and from about 2.5 to 4.0 mol. % orthoxylene using a fluidized bed. Although higher concentrations may be employed, explosive hazards may be encountered. Lower concentrations of orthoxylene less than about 1%, of course, will reduce the production rate obtained at equivalent flow rates and thus are not normally economically employed.

Flow rates of the gaseous feedstream typically will be sufficient to provide a contact time with the catalyst of from about 0.5 to about 5, preferably from about 0.5 to about 3.5, most preferably from about 0.5 to about 2.5 seconds. At contact times of less than about 0.5 seconds, less efficient operations are obtained. The hourly loading of the catalyst in a tube having a diameter of 25 mm and a length of 3 meters is generally from about 2000 to 6000 liters of air with about 20 to 150 g. of orthoxylene per 1000 liters of air.

A variety of reactors will be found to be useful and multiple tube heat exchanger type reactors are quite satisfactory. The tubes of such reactors may vary in diameter typically from about 20 to 50 mm, and the length may be varied from about 1 to 5 meters.

The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Various heat conductive materials may be employed, but it has been found that eutectic salt baths are completely satisfactory. One such salt bath is described below and is a eutectic constant temperature mixture. As will be recognized by one skilled in the art, the heat exchange medium may be kept at the proper temperature by heat exchangers and the like. The reactor or reaction tubes may be stainless steel, carbon steel, nickel, carbon-glass tubes such as Vycor and the like. Both carbon-steel and nickel tubes have excellent long life under the conditions of the reactions described herein.

Optionally, the reactors contain a preheat zone of an inert material such as ¼ inch Alundum pellets, inert ceramic balls, metallic balls or chips and the like, present at about ½ to 1/10 the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the orthoxylene concentration. Under usual operating conditions, in compliance with the preferred procedure of this invention, the average bed temperature referred to herein as the reaction temperature, measured by thermocouples disposed in the reactor, is typically from about 300° to about 500° C., preferably from about 320° to about 440° C., and most preferably from about 330° to about 420° C. Under normal conditions, the temperature in the reactor ordinarily should not be allowed to go above about 525° C. for extended lengths of time because of decreased yields and possible deactivation of the novel catalyst of this invention.

The reaction may be conducted at atmospheric, superatmospheric or below atmospheric pressure, with pressure of from 1 to 20 psig being generally entirely suitable.

The phthalic anhydride may be recovered by a number of ways well known to those skilled in the art. For example, the recovery may be by direct condensation or by absorption in suitable media, with subsequent separation and purification of the phthalic anhydride. By-products such as tolualdehyde, phthalide, and maleic anhydride may also be formed, and can be separated from the phthalic anhydride by conventional means. If desired the purified phthalic anhydride can be reacted with an organic alcohol (such as an oxo-alcohol, e.g., isodecyl alcohol) to prepare phthalate esters which find use as plasticizers.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples, the reactor used to test the catalyst is described as follows:

The reactor tube for the catalyst bed was fabricated from 316 stainless steel and had a ½-inch outside diameter, a wall thickness of 0.049 inch and a length of 12 inches. The bottom of the reactor tube was charged with 2 cc of 3 mm glass beads (VICOR ® beads), and then about 2 gm. of unsupported catalyst, having an average particle size of about 0.5 mm and premixed with about 15 g (8 ml) of 0.55 mm glass beads (VICOR ® beads), was charged to the reactor as the catalyst bed. On top of the catalyst bed was then placed 2 cc of 3 mm glass beads (VICOR ® beads). A ⅛-inch stainless steel thermowell tube was provided down the center of the reactor tube, and a thermocouple was provided within the thermowell for measurement of catalyst bed temperatures along the length of the reactor. The reactor tube was immersed in a HITEC ® salt bath. The reactor inlet pressure as about 1 psig. The orthoxylene feed was caused to pass through the reactor tube in an upflow manner. Once a catalyst evaluation was started the reaction was continued for the longer of the selected run time or 8 hours. At the conclusion of each run, the catalyst, if to be used again, was kept under nitrogen purge at a temperature of from about 320° to 330° C. Analyses of reactor effluent gas were made at convenient time intervals by gas chromatography. Carbon balance was calculated according to the number of gram atoms of carbon in the reactor effluent to the gram atoms of carbon fed to the system.

Conversion of orthoxylene is calculated according to the following equation:

$$\% \text{ o-xylene conversion} = \frac{\text{g-moles of reacted o-xylene}}{\text{g-moles of o-xylene feed}} \times 100$$

Phthalic anhydride yield is calculated according to the following equation:

$$\% \text{ PAN yield} = \frac{\text{g-moles of PAN produced}}{\text{g-moles of o-xylene feed}} \times 100$$

The selectivity of phthalic anhydride is calculated according to the following equation:

$$\% \text{ selectivity to PAN} = \frac{\text{g-moles of PAN produced}}{\text{g-moles of o-xylene reacted}} \times 100$$

(% selectivity to intermediate oxidation products (e.g., tolualdehyde, phthalide) is calculated as shown above.)

In the Examples, the $TiO_2$ (Mobay) anatase charged was determined by atomic absorption analysis to contain about 0.15 wt. % K, 0.10 wt. % P, 0.10 wt. % Al and 0.16 wt. % Si (calculated as the respective elements) all of which are believed to be present as the corresponding metal oxides in the calcined catalysts prepared as described below. All Examples used $TiO_2$ (Mobay), 100% anatase, specific surface area of 9 $m^2$/gm, pore size of 150–250 um; −60+ −200 mesh. All amounts are weight % unless otherwise indicated.

EXAMPLE

Preparation of Catalyst

Catalyst A: 7% $V_2O_5$/0.2% $MoO_3$ on $TiO_2$

To 24.65 grams of titanium dioxide anatase powder dispersed in 20 ml. of $H_2O$ was added 0.06 gram of ammonia heptamolybdate ($MoO_3 = 81.5\%$). The resulting mixture was heated with stirring at 110° C. for 16 hours, then calcined at 450° C. in $O_2$ for 2 hours. The catalyst sample was then sieved to −100 mesh powder. A 17.19 gram portion of the resulting calcined powder was then impregnated with 40 ml of an aqueous solution containing 1.24 grams $V_2O_5$, 2.85 grams oxalic acid and 6.47 grams formamide, followed by concentration at 65° C. in air, oven drying at 110° C. and calcining in a flowing oxygen atmosphere at 450° C. for 2 hours.

The resulting solids were then crushed into −20+40 mesh particles. The thus formed catalyst was determined by calculation (based on the quantity of vanadium and molybdenum so impregnated thereon) to comprise 7 wt. % $V_2O_5$ and 0.2 wt. % molybdenum trioxide on $TiO_2$.

Catalyst B: 7%$V_2O_5$/0.5% $WO_3$ on $TiO_2$

To 22.92 grams of titanium dioxide anatase powder dispersed in 80 ml. of water was added 0.125 gram of ammonium metatungstate having a purity of 92.59%. The resulting mixture was heated with stirring at 110° C. for 16 hours for drying then calcined at 450° C. in $O_2$ for 2 hours. The catalyst sample was then sieved to −100 mesh powder. A 15.31 gram portion of the resulting calcined powder was then impregnated with 40 ml of an aqueous solution containing 1.15 grams $V_2O_5$, 2.53 grams oxalic acid and 5.76 grams formamide, followed by concentration at 65° C. in air, oven drying at 110° C. and calcining in a flowing oxygen atmosphere at 450° C. for 2 hours.

The resulting solids were then crushed into −20+40 mesh particles. The thus formed catalyst was determined by calculation (based on the quantity of vanadium and tungsten so impregnated thereon) to comprise 7 wt. % $V_2O_5$ and 0.5 wt. %, tungsten trioxide on $TiO_2$.

Comparative Catalyst C: 7%$V_2O_5$ on $TiO_2$

To 40 ml of water is added 0.75 gram of vanadium pentoxide, 1.65 grams of oxalic acid and 3.75 grams of formamide at room temperature with stirring to form vanadium oxalate, and this solution was then mixed with 10.0 grams of titanium dioxide anatase powder (which were first dispersed in 20 ml of water). The resulting mixture was heated with stirring at 65° C. to evaporate the majority of the water, followed by drying in an oven (101 kPa) at 110° C. for 16 hours. The resulting solid was then calcined in a flowing oxygen gas stream at 450° C. for 2 hours, followed by crushing and screening to form −20+40 mesh particle size. The catalyst formed by the above impregnation procedure was determined by calculation (based on the vanadium salt and the weight of the titanium dioxide particles) to contain 7 wt. % $V_2O_5$ on the $TiO_2$.

Preparation of Phthalic Anhydride

Employing the reactor and process conditions indicated, Catalysts A and B and Comparative Catalyst C prepared as above were charged to the reactor tube in separate runs to determine their activity for the partial oxidation of orthoxylene to phthalic anhydride. The data thereby obtained for each catalyst are set forth in Table I below.

From the data presented in the accompanying Table, and from the FIGURE, it can be seen that the performance of Catalysts A and B of the present invention with respect to phthalic anhydride selectivity at 100% o-xylene conversion, was superior to that of Comparative Catalyst C.

TABLE I

| Catalyst | Temp. (°C.) | Run[1] Time (hrs) | o-xylene Conversion (mol %) | PAN Yield (mol %) | PAN Yield (wt %) | Selectives (mol. %) to: PAN | Tol | Ph |
|---|---|---|---|---|---|---|---|---|
| A | 340 | 5.1 | 97.0 | 73.7 | 102.8 | 76 | 0.2 | 0 |
|   | 338 | 3.1 | 97.9 | 74.8 | 104.3 | 76.4 | 0.3 | 0 |
|   | 333 | 2.8 | 77.7 | 57.7 | 80.5 | 74.3 | 2.0 | 1.2 |
|   | 326 | 3.2 | 58.5 | 40.7 | 56.7 | 69.5 | 4.5 | 2.9 |
|   | 338 | 3.8 | 97.6 | 74.7 | 104.2 | 76.5 | 0.2 | 0 |
|   | 339 | 2.9 | 100 | 76.0 | 106.0 | 76.0 | 0 | 0 |
| B | 341 | 5.5 | 100 | 75.9 | 105.9 | 75.9 | 0 | 0 |
|   | 336 | 3.8 | 75.6 | 52.8 | 73.7 | 69.9 | 2.5 | 2.2 |
|   | 331 | 3.2 | 61.6 | 40.2 | 56.0 | 65.2 | 4.0 | 3.8 |
|   | 340 | 2.9 | 100 | 75.7 | 105.6 | 75.7 | 0 | 0 |
| C (Comparative) | 343 | 5.0 | 98.4 | 73.4 | 102.4 | 74.6 | 0 | 0 |
|   | 339 | 8.0 | 100 | 73.6 | 102.7 | 73.6 | 0 | 0 |
|   | 321 | 3.6 | 60 | 44.8 | 62.5 | 74.6 | 3.8 | 2.4 |
|   | 326 | 2.6 | 74 | 57.3 | 79.9 | 77.4 | 2.2 | 1.3 |
|   | 332 | 2.4 | 94 | 72.0 | 100.4 | 76.6 | 0.6 | 0 |

Notes:
"PAN" - phthalic anhydride; "Tol" - tolualdehyde; "Ph" - phthalide
[1]vapor feed to reactor = 1.25 mol % o-xylene in air; space velocity = 2760 hr$^{-1}$.

What is claimed is:

1. A process for the preparation of a carboxylic anhydride comprising reacting a hydrocarbon with molecular oxygen in the vapor phase, in the presence of a solid oxidation catalyst, said solid oxidation catalyst being obtained by the steps of:
    (a) forming a catalyst precursor by depositing on titanium dioxide in the anatase form, a discontinuous monolayer amount of at least one Group VIB metal oxide source which is convertible to the Group VIB metal oxide upon calcining;
    (b) calcining said catalyst precursor under conditions sufficient to convert said Group VIB metal oxide source into the Group VIB metal oxide in an amount sufficient to deposit from about 0.05 to 1.0 wt. % of Group VIB metal oxide;
    (c) depositing upon the calcined catalyst precursor a catalytically effective amount of at least one vanadium oxide source which is convertible to vanadium oxide upon calcining; and
    (d) calcining the catalyst solids formed in step (c) under conditions sufficient to convert said vanadium compound to vanadium oxide in an amount defined by a vanadium: Group VIB metal atomic ratio of from about 5:1 to 20,000:1.

2. The process according to claim 1 wherein said catalyst precursor is calcined in step (b) at a temperature of from about 150° to 750° C.

3. The process according to claim 2 wherein said calcining is effected for a time of from about 0.5 to 16 hours.

4. The process according to claim 1 wherein said Group VIB metal oxide source comprises at least one member selected from the group consisting of Group VIB metal halides, phosphates, oxides, carbonates, sulfates, alkoxides, nitrates, hydroxides, carboxylates and oxy halides.

5. The process according to claim 1 wherein said Group VIB metal oxide source comprises a compound selected from ammonium metatungstate, tungsten halides and tungsten oxyhalides.

6. The process according to claim 1 wherein said Group VIB metal oxide source comprises a compound selected from ammonium heptabmolybdate, molybdenum halides and molybdenum oxyhalides.

7. The process according to claim 1 wherein said Group VIB metal oxide source comprises a compound selected from chromium halides, chromium nitrate, chromium perchlorate, chromium sulfate and chromium pentadionate.

8. The process according to claim 1 wherein said vanadium source comprises at least one compound selected from the group consisting of vanadium pentoxide, ammonium metavanadate, vanadyl sulfate, vanadyl chloride, vanadyl dichloride, metavanatic acid, pyrovanatic acid, vanadium hydroxide, vanadyl oxalate and vanadyl carboxylate.

9. The process according to claim 1 wherein said catalyst, following calcination according to step (d), is characterized by specific surface area of less than 50 square meters per gram.

10. The process according to claim 1 wherein said hydrocarbon comprises at least one member selected from the group consisting of orthoxylene and naphthalene, and wherein said carboxylic anhydride comprises phthalic anhydride.

11. The process according to claim 10 wherein said orthoxylene or naphthalene feed is passed to a reaction zone containing said solid oxidation catalyst at a mass flow rate of from about 20 to 150 grams per Nm³ under vapor phase conditions, said reaction being effected at a temperature of from about 200° to 500° C.

12. The process according to claim 1 wherein said hydrocarbon comprises durene and wherein said carboxylic anhydride comprises pyromellitic dianhydride.

13. The process according to claim 12 wherein said durene is passed to a reaction zone containing said solid oxidation catalyst under vapor phase reaction conditions and at a durene feed rate of from about 5 to 100 grams per Nm³, and said reaction is effected at a temperature within the range of from about 300° to 500° C.

14. The process according to claim 1 wherein said Group VIB metal oxide source is deposited on said titanium dioxide in an amount sufficient about 0.10 to 0.50 wt. % of Group VIB, metal oxides, deposited on the titanium dioxide.

15. The process according to claim 1 wherein said vanadium oxide source is deposited upon said calcined catalyst precursor in an amount sufficient to provide at least $N_{min}$ grams of $V_2O_5$, wherein $$N_{min} = (G) \times (A) \times (0.0007)$$

wherein "G" is the grams of said calcined catalyst precursor and "A" is the specific surface area of said calcined catalyst precursor.

16. The process according to claim 11 wherein said vanadium oxide source is deposited on said calcined catalyst precursor in an amount sufficient to provide at least about 1.7 $N_{min}$ grams of $V_2O_5$.

17. The process according to claim 14 wherein said hydrocarbon comprises at least one member selected from the group consisting of orthoxylene and naphthalene, and wherein said carboxylic anhydride comprises phthalic anhydride.

18. The process according to claim 15 wherein orthoxylene or napthalene feed is passed to a reaction zone containing said solid oxidation catalyst under vapor phase reaction conditions and at a mass flow rate of from about 20 to 150 grams per Nm³, and said reaction is effected at a temperature of from about 200° to 500° C.

* * * * *